United States Patent [19]

Anderson et al.

[11] Patent Number: 5,008,193

[45] Date of Patent: * Apr. 16, 1991

[54] ASCORBIC ACID INTERMEDIATES AND PROCESS ENZYMES

[75] Inventors: Stephen Anderson; David R. Light, both of San Mateo; Cara Marks, San Francisco; William H. Rastetter, Rancho Santa Fe, all of Calif.

[73] Assignee: Genentech, Inc., So. San Francisco, Calif.

[*] Notice: The portion of the term of this patent subsequent to Jul. 12, 2005 has been disclaimed.

[21] Appl. No.: 53,290

[22] Filed: May 21, 1987

Related U.S. Application Data

[63] Continuation-in-part of Ser. No. 620,585, Jun. 14, 1984, abandoned, which is a continuation-in-part of Ser. No. 508,410, Jun. 28, 1983, abandoned.

[51] Int. Cl.$^5$ .................... C12P 7/60; C12P 19/34; C12N 9/04; C12N 15/00; C12N 1/00; C12N 1/13

[52] U.S. Cl. ................... 435/138; 435/190; 435/172.3; 435/91; 435/843; 435/320.1; 435/847; 435/823; 435/252.32; 435/252.3

[58] Field of Search .............. 435/138, 190, 172.3, 435/91, 320, 823, 843, 847, 252.3; 935/14, 29, 42, 66

[56] References Cited

U.S. PATENT DOCUMENTS 3,790,444  2/1974  Oga et al. .
3,907,639  9/1975  Makover et al. .
4,245,049  1/1981  Kita et al. .
4,263,402  4/1981  Kita et al. .
4,316,960  2/1982  Kita et al. .
4,543,331  9/1985  Sonoyama et al. .
4,757,012  7/1988  Estell et al. .................... 435/320
4,758,514  7/1988  Light et al. .................... 435/190

FOREIGN PATENT DOCUMENTS 0046284  8/1981  European Pat. Off. .
0088409  3/1983  European Pat. Off. .

OTHER PUBLICATIONS

Sonoyama et al., "Production of 2-Keto-L-Gulonic Acid from D-Glucose by Two-Stage Fermentation", Applied and Environmental Microbiology, vol. 43, No. 5, May 1982, pp. 1064–1069.

Adachi et al., "Crystallization and Characterization of NADP-Dependent D-Glucose Dehydrogenase from *Gluconobacter suboxydans*", Agric. Biol. Chem., 44(2), 1980, pp. 301–308.

*Primary Examiner*—Charles F. Warren
*Assistant Examiner*—Christopher S. F. Low
*Attorney, Agent, or Firm*—Ginger R. Dreger

[57] ABSTRACT

Methods for producing ascorbic acid using recombinant means comprising the transfer of genetic material by conjugation, a host cell lacking, entirely or to such an extent as not to be commercially useful, one or more enzymes in the metabolic path converting glucose to 2 keto-L-gulonic acid.

12 Claims, 7 Drawing Sheets

EXPRESSION VECTOR FOR CORYNEBACTERIUM 2,5-DKG REDUCTASE

ASCORBIC ACID INTERMEDIATES AND PROCESS ENZYMES

This application is a continuation-in-part of Ser. No. 06/620,585, filed June 14, 1984, which was a continuation-in-part of Ser. No. 06/508,410, filed June 28, 1983, now abandoned. Cross reference is made to application Ser. No. 06/620,651, filed June 14, 1984, now U.S. Pat. No. 4,757,012, which is a continuation-in-part of application Ser. No. 06/508,628, filed June 28, 1983, now abandoned and to Ser. No. 06/620,652, filed June 14, 1984, now U.S. Pat. No. 4,758,514, which is a continuation-in-part of application Ser. No. 06/508,409, filed June 28, 1983, now abandoned.

BACKGROUND

This invention concerns aspects of a process for production of ascorbic acid. It specifically relates to purification of a useful protein, to production of proteins using recombinant techniques and to the use of such proteins in chemical conversions. More particularly, the invention relates to purification of and recombinant production of 2,5-diketogluconic acid (2,5-DKG) reductase and the use of the reductase so produced in converting 2,5-DKG stereoselectively into 2-keto-L-gulonic acid (2-KLG), as well as to the production of a single recombinant organism capable of synthesizing 2-KLG. The 2-KLG produced is a useful intermediate in the production of ascorbic acid (vitamin C).

Ascorbic acid has become a major chemical product in the United States, and elsewhere in the world, due to its importance in health maintenance. While there may be some controversy over its efficacy in ameliorating the tendency of individuals to contract certain minor illnesses such as for example. the common cold, there is no doubt that it is essential for human beings to ingest required amounts of vitamin C. It has become a matter of concern in recent years that "natural" foods may not provide adequate amounts of vitamin C. Accordingly, there has developed a large demand for ascorbic acid, both as an additive to foods which are marketed to the consumer with supplemented levels of this vitamin, and as a direct vitamin supplement. Furthermore, ascorbic acid is an effective antioxidant and thus finds applications as a preservative both in nutritional and in other products.

There are a number of processes available, some commercially viable, for the production of vitamin C. Several of these result in the preliminary production of 2-keto-L-gulonic acid (2-KLG) which can then be rather simply converted to ascorbic acid through acid or base catalyzed cyclization. Accordingly, 2-KLG has become, in itself a material of considerable economic and industrial importance.

Means are presently available in the art to convert relatively plentiful ordinary metabolites, such as, for example, D-glucose, into 2,5-diketogluconic acid (2,5-DKG) by processes involving the metabolism of prokaryotic microorganisms. See, for example, U.S. Pat. Nos. 3,790,444 (Feb. 5, 1974); 3,998,697 (Dec. 21, 1976); and EPO Application Publication No. 0046284 published Feb. 24, 1982. The availability of this 2,5-DKG intermediate offers a starting material which is converted to the desired 2-KLG only by the single step of a two electron reduction. The reduction can be effected chemically or catalyzed enzymatically. Various bacterial strains are known which are capable of effecting this reduction. Such strains are found in the genera Brevibacterium, Arthrobacter, Micrococcus, Staphylococcus, Pseudomonas, Bacillus, Citrobacter and Corynebacterium. See for example, U.S. Pat. Nos. 3,922,194 (Nov. 25, 1975), 4,245,049 (Jan. 13, 1981) and 3,959,076 (May 25, 1976). Such strains have indeed been used to effect this reduction; however, use of such strains per se without enzyme purification does not permit certain alternative approaches available with the use of purified enzyme. Such a system would permit, for example, continuous production through immobilization of the enzyme on a solid support. Further, access to the genetic machinery to produce such an enzyme permits manipulation and localization to achieve production of the enzyme at a site most convenient for the conversion of 2,5-DKG. Most important among such loci is a site within the same organism which is capable of effecting the production of 2,5-DKG. Thus, a single organism would use its own machinery to manufacture the 2,5-DKG in situ and then using the 2,5-DKG reductase gene provided through recombinant technology produce the desired product.

It is helpful to understand the context into which the present invention finds utility, by representing the process in terms of the relevant chemical conversions. An outline of a typical overall process for manufacture of ascorbic acid is shown in Reaction Scheme 1.

Reaction Scheme 1

The process conveniently begins with a metabolite ordinarily used by a microorganism such as, for example, D-glucose as shown in Reaction Scheme 1. Through enzymatic conversions, which may include the enzymes D-glucose dehydrogenase, D-gluconate dehydrogenase and 2-keto-D-gluconate dehydrogenase, the D-glucose undergoes a series of oxidative steps to give 2,5-diketo-D-gluconic acid. It has been shown that this series of steps can be carried out in a single organism. (U.S. Pat. No. 3,790,444, EPO Appln. A20046284

[supra]); such organisms are, for example, of the genus Gluconobacter, Acetobacter or Erwinia.

Alternate preparations of ascorbic acid have circumvented the 2,5-DKG intermediate by a combination of fermentative and chemical oxidations, and are clearly more cumbersome than the process shown. Typical of these is the Reichstein synthesis which utilizes diacetone-2-keto-L-gulonic acid as a precursor to 2-KLG. This intermediate is generated through a series of reductive and oxidative steps involving fermentation, hydrogenation, and, e.g., permanganate oxidation. Such a sequence is more complex than the reaction scheme shown above. The conversion of 2,5-DKG into 2-KLG can also be carried out enzymatically (U.S. Pat. Nos. 3,922,194; 3,959,076 [supra]; and 4,245,049 [Jan. 13, 1981]).

Means are presently well known in the art to convert the resulting 2-KLG into ascorbic acid. This may be done either in the presence of dilute acid and heat or in a two-step process utilizing preliminary esterification in methanol, followed by lactonization in base. Effective procedures are described in Crawford, T. C., et al., Advances in Carbohydrate Chemistry and Biochemistry, 37, 79–155 (1980). These alternatives are straightforward and take advantage of the greater stability and shelf life of 2-KLG over ascorbic acid. Thus, it is more desirable and convenient to stockpile the 2-KLG intermediate for subsequent conversion to the desired final product than to synthesize the ascorbic acid directly.

Because of the improvements of the present invention, alternate, superior means are available to effect certain aspects of this overall conversion. In one approach, because the enzyme responsible for the conversion of 2,5-DKG into 2-KLG has been isolated and purified, the reduction step can be carried out under more controlled conditions, including those whereby the enzyme is immobilized and the solution substrates are fed continuously over the immobilized catalyst. In addition, the availability of recombinant techniques makes possible the production of large amounts of such enzyme available for ready purification. Further, recombinant techniques permit the coding sequences and necessary expression control mechanisms to be transferred into suitable host organisms with improved characteristics. Thus, simply focusing on the conversion of 2,5-DKG to 2-KLG, three levels of improvement are attainable: (1) stricter control over variables; (2) availability of continuous processing; and (3) selection of host organism for the enzyme which has desirable qualities pertinent to the reduction reaction.

The scope of improvement permitted by the effective cloning and expression of the 2,5-DKG reductase is, however even broader. Because of the availability of the appropriate genetic machinery, it is possible, as well as desirable, to transform an organism which is capable of producing the 2,5-DKG with the gene encoding the reductase. Thus, the same organism can effect the entire process of converting, for example, glucose or other suitable ordinary metabolite into the stable, storable intermediate 2-KLG.

SUMMARY OF THE INVENTION

The present invention effects dramatic improvements in the process for converting a commonly available metabolite such as glucose into 2-KLG, a stable storable precursor for ascorbic acid. The pathway of the process described by the present invention encompasses the step of converting 2,5-DKG into 2-KLG. The current processes for formation of the 2-KLG intermediate involve, at best, the deployment of at least two organisms or killed cultures thereof, do not permit regulation of the enzyme levels available, and are limited to batchwise processes.

Another aspect of the invention is a process for the construction of a recombinant expression vector for the production of 2,5-DKG reductase. Still another aspect includes the expression vector so produced, cells and cell cultures transformed with it, and the product of such cells and cell cultures capable of effecting the reduction of 2,5-DKG stereospecifically to 2-KLG. Still another facet of this aspect of the invention is a process for converting 2,5-DKG to 2-KLG using recombinant reductase.

Finally, the invention also relates to a process for converting glucose or other ordinary microbial metabolite into 2-KLG by fermentation by a single recombinant organism and thereafter to ascorbic acid. It also relates to the recombinant organism, and thereafter to ascorbic acid. It also relates to particular microorganisms that may be transformed using the process of conjugation. It also relates to the recombinant organism capable of carrying out the conversion of glucose or other ordinary metabolite to 2-KLG. Such an organism is conveniently constructed by transferring to a host cell capable of effecting the conversion of the initial metabolite to 2,5-DKG an expression vector encoding and capable of expressing the sequence for the 2,5-DKG reductase. Alternatively, such a recombinant organism is constructed by transforming an organism already producing the 2,5-DKG reductase with vectors encoding the enzymes responsible for the oxidation of metabolite to 2,5-DKG. In either event, use of proper promoters and ribosome binding sites within the construction of the expression vectors permits the expression of the gene or genes for the enzyme(s) in the host cell.

DETAILED DESCRIPTION

A. Definitions

As used herein, "2,5-DKG reductase" refers to a protein which is capable of catalyzing the conversion of 2,5-DKG stereoselectively to 2-KLG. Many species have been found to contain the reductase particularly members of the coryneform group, including the genera Corynebacterium, Brevibacterium, and Arthrobacter; hence it appears by virtue of present knowledge that a preferred source for the enzyme is a member of the coryneform group. In the specific example herein, the particular form of this enzyme present in Corynebacterium was cloned and expressed. However, other bacterial species, such as, for example, those from the genera Brevibacterium, Arthrobacter, Micrococcus, Staphylococcus, Pseudomonas, Citrobacter and Bacillus are also known to synthesize an enzyme with the same activity as this enzyme. These genera are illustrative of potential sources for an enzyme similar to that present in Corynebacterium which may be available to catalyze this conversion. Alternate sources in addition to these naturally occurring ones in the prokaryotic kingdom may well be found. In addition, as the invention herein discloses and makes available the genetic sequence encoding such enzymes, modifications of the sequence which do not interfere with, and may, in fact, improve the performance of this enzyme are also available to those knowledgeable in the art. Such modifications and altered sequences are included in the definition of 2,5-DKG reductase as used in this specification. In short, the term 2,5-DKG reductase has a functional definition and refers to any enzyme which catalyzes the conversion of 2,5-DKG to 2-KLG.

It is well understood in the art that many of the compounds discussed in the instant specification, such as proteins and the acidic derivatives of saccharides, may exist in variety of ionization states depending upon their surrounding media, if in solution, or out of the solutions from which they are prepared if in solid form. The use of a term such as, for example, gluconic acid, to designate such molecules is intended to include all ionization states of the organic molecule referred to. Thus, for example, both "D-gluconic acid" and "D-gluconate" refer to the same organic moiety, and are not intended to specify particular ionization states. It is well known that D-gluconic acid can exist in unionized form, or may be available as, for example, the sodium, potassium, or other salt. The ionized or unionized form in which the compound is pertinent to the disclosure will either be apparent from the context to one skilled in the art or will be irrelevant. Thus, the 2,5-DKG reductase protein itself may exist in a variety of ionization states depending on pH. All of these ionization states are encompassed by the term "2,5-DKG reductase."

Similarly, "cells" and "cell cultures" are used interchangeably unless the context indicates otherwise. Gene transfer refers to a transfer or exchange of genetic material from one source to a recipient. There are three frequently used methods of gene transfer in bacteria: transformation (sometimes referred to as transfection), transduction and conjugation. Other gene transfer techniques are protoplast fusion and R' plasmids (Holloway, B. W., J. Bacteriol. 133:1078 [1978]). The transfer of a gene to a cell or to cells comprising a cell culture amounts to the same activity; it is a gene transfer process in which exogenously added DNA is taken up by a bacterium. A cell or microorganism receiving the transferred gene by one of the three types of gene transfer that now replicates and expresses the DNA so taken up is referred to as a recipient cell or microorganism. It is each bacterium that takes up the transferred material, frequently an expression vector, although it is a culture of bacteria that is treated with the genetic material.

"Transduction" refers to a gene transfer process in which a bacterial virus propagating on one strain of bacterium, the donor, picks up genetic information and upon infection of another strain of bacterium, the recipient, sometimes causes a heritable change. A recipient cell that acquires a donor trait by this process is called a transductant. "Conjugation" refers to a gene transfer process in which one strain of bacterium, the donor, possessing a conjugative plasmid, makes physical contact with another strain of bacterium, the recipient, and transfers genetic material. Conjugative plasmids possess "tra" genes that typically specify and/or control: synthesis of appendages referred to as donor pili, which allow donor cells to make contact with recipient cells; synthesis and release of substances that minimize donor-donor matings; and, conjugational transfer of DNA commencing from a definable transfer origin site on the conjugative plasmid molecule. The recipient which acquires donor genetic information is called a transconjugant. Strains with readily selectable genetic markers such as nalidixic acid or rifampicin resistance, or special nutritional requirements, are used in order to isolate transconjugants. "Transformation" refers to a gene transfer process carried out by various methods such as by nuclear injection or calcium treatment using calcium chloride as described by Cohen, F. N. et al., Proc. Natl. Acad. Sci. U.S.A. 69:2110 (1972).

"Expression vector" includes vectors which are capable of expressing DNA sequences contained therein where such sequences are operably linked to other sequences capable of effecting their expression. It is implied, although not explicitly stated, that expression vectors must be replicable in the host organisms either as episomes or as an integral part of a chromosomal DNA; clearly a lack of replication would render them effectively inoperable. In sum, "expression vector" is also given a functional definition. Generally, expression vectors of utility in recombinant techniques are often in the form of "plasmids," which term refers to circular double stranded DNA molecules which, in their vector form are not linked to the chromosomes. Other effective vectors commonly used are phage and non-circular DNA. In the present specification, "plasmid" and "vector" are often used interchangeably, however, the invention is intended to include such other forms of expression vectors which serve equivalent functions and which are, or subsequently become, known.

"Recombinant cells" refers to cells into which vectors, constructed using recombinant DNA techniques, have been introduced using one of the methods described above. "Host" cells refers to such cells before the DNA has been transferred. In general, recombinant cells produce protein products encoded by such recombinant vectors which protein products would not ordinarily be produced; however, the definition also includes cells containing vectors encoding proteins which are, coincidentally, encoded in the bacterial chromosome or otherwise endogenously expressed in the recipient cell. The definition includes any cell which is producing the product of a xenogeneic sequence by virtue of recombinant techniques.

"Ordinary metabolite" refers to such carbon sources as are commonly utilized by bacteria for growth. Examples of such metabolites are glucose, galactose, lactose, fructose or other carbohydrates which are readily available foodstuffs for such organisms. Such metabolites are defined herein to include enzymatic derivatives of such foodstuffs which are convertible into 2,5-diketo-D-gluconic acid. Such derivatives include D-gluconic acid, D-mannonic acid, L-gulonic acid, L-idonic acid, 2-keto-D-gluconic acid, 5-keto-D-gluconic acid, and 5-keto-D-mannonic acid.

B.1 Cloning and Expression of 2,5-DKG Reductase

Both the availability of large amounts of purified 2,5-DKG reductase and its ability to be generated in situ in an organism which makes 2,5-DKG is greatly aided by the process of the invention which provides a means for cloning and expression of the gene for the reductase enzyme. The general procedure by which this is accomplished is summarized as follows, and a specific example of such procedures is outlined herein below in Example 1.

The gene encoding 2,5-DKG reductase is cloned in either plasmid or phage vehicles from a genomic library created by partially digesting high molecular weight DNA from Corynebacterium or other suitable source using a restriction enzyme. For 2,5-DKG reductase, a suitable restriction enzyme is Sau 3A. Alternatively, a limited digest with a restriction enzyme having greater specificity, such as BamHI or PstI, may be used. The restriction digest is then ligated either to plasmid vectors replicable in suitable bacterial hosts, or to phage sequences capable of propagation in convenient bacterial cultures. The resulting plasmid and phage libraries are then screened using probes constructed based on the known partial sequence of the 2,5-DKG reductase protein (see European Patent Application No. 84304277.1). The efficiency of probe design may be improved by selecting for probe construction those codons which are known to be preferred by bacterial hosts. Identification of the desired clones from the plasmid and phage libraries is best effected by a set of probes such that the desired gene will hybridize to all of the probes under suitable stringency conditions and false positives from the use of only one probe eliminated. Upon recovery of colonies or phage successful in hybridizing with the oligonucleotides provided as probes, identity of the sequence with the desired gene is confirmed by direct sequencing of the DNA and by in vivo expression to yield the desired enzyme.

The complete functional gene is ligated into a suitable expression vector containing a promoter and ribosome binding site operable in the host cell into which the coding sequence will be transformed. In the current state of the art, there are a number of promotion/control systems and suitable prokaryotic hosts available which are appropriate to the present invention. Similar hosts can be used both for cloning and for expression since prokaryotes are, in general, preferred for cloning of DNA sequences, and the method of 2-KLG production is most conveniently associated with such microbial systems. *E. coli* K12 strain 294 (ATCC No. 31446) is particularly useful as a cloning host. Other microbial strains which may be used include *E. coli* strains such as *E. coli* B, *E. coli* X1776 (ATCC No. 31537) and *E. coli* DH-1 (ATCC No. 33849). For expression, the aforementioned strains, as well as *E. coli* W3110 (F−, λ−, prototrophic ATCC No. 27325), bacilli such as *Bacillus subtilus*, and other enterobacteriaceae such as *Salmonella typhimurium* or *Serratia marcesans*, and various Pseudomonas species may be used. A particularly preferred group of hosts includes those cultures which are capable of converting glucose or other commonly available metabolites to 2,5-DKG. Examples of such hosts are generally found among the genera Acetobacter, Gluconobacter, Acetomonas and Erwinia. The taxonomy and nomenclature of these genera are such that the same or similar strains are sometimes given different names. For example, *Acetobacter cerinus* used in the example below is also referred to as *Gluconobacter cerinus*. Examples of particular hosts include, but are not limited to, *Erwinia herbicola* ATCC No. 21998 (also considered an *Acetomonas albosesamae* in U.S. Pat. No. 3,998,697); *Acetobacter (Gluconobacter) oxydans* subspecies melanozenes, IFO 3292, 3293 ATCC No. 9937; *Acetobacter (Gluconobacter) cerinus* IFO 3263 IFO 3266; *Gluconobacter rubiginosus*, IFO 3244; Acetobacter Fragum ATCC No. 21409; *Acetobacter (Acetomonas)* suboxydans subspecies industrious ATCC No. 23776.

In general, plasmid expression or cloning vectors or conjugative plasmids containing replication and control sequences which are derived from species compatible with the host cell are used in connection with these hosts. The vector ordinarily carries a replication site, as well as marking sequences which are capable of providing phenotypic selection in transformed cells. For example *E. coli* is typically transformed using pBR322, a plasmid derived from an *E. coli* strain (Bolivar, et al., Gene 2: 95 (1977)). pBR322 contains genes for ampicillin and tetracycline resistance and thus provides easy means for identifying transformed cells. For use in expression, the pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al,, Nature, 275: 615 [1978]; Itakura et al., Science 198: 1056 [1977]; Goeddel et al., Nature 281: 544 [1979]) and a tryptophan (trp) promoter system (Goeddel et al., Nucleic Acids Res., 8: 4057 [1980]; EPO Application No. 0036776). While these are the most commonly used, other microbial promoters have been discovered and utilized, and details concerning their nucleotide sequences have been published, enabling a skilled worker to ligate them functionally in operable relationship to genes in transformation vectors (Siebenlist et al., Cell 20: 269 [1980]).

By suitable cleavage and ligation DNA sequences encoding 2,5-DKG reductase can be included in the aforementioned vectors prepared as outlined above. Any unnecessary or inhibitory sequences may be deleted and the prokaryotic enzyme may then be purified; or the intact or broken cells used directly as catalysts; or alternatively, the host may be chosen so that once transformed it is capable of effecting the entire conversion of glucose or other suitable metabolite to the desired 2-KLG product.

B.2 Conversion of Glucose or Other Metabolite to 2-KLG by a Single Recombinant Organism The availability of recombinant techniques to effect expression of enzymes in foreign hosts permits the achievement of the aspect of the invention which envisions production of 2-KLG in a single host organism from a readily available metabolite. This method has considerable advantage over presently used methods in that a single viable organism fermentation is substituted for two fermentations, and there is at least a partial balance of the oxidizing and reducing equivalents required for this conversion. At present there is no naturally occurring organism which is known to be capable of catalysis of this entire sequence of steps such that 2-KLG is produced in usable quantities. Certain wild type organisms may produce 2-KLG however the level produced is not sufficient to be economically practical. It has been observed that wild type *A. cerinus* (IFO 3263) has its own cytoplasmic 2,5 DKG reductase enabling the organism to convert glucose to 2-KLG at a level of approximately 0.2 g/l under controlled conditions. Under the same controlled conditions and using the method of this invention, described below, a plasmid capable of expressing 2,5 DKG reductase can be transferred to *A. cerinus* (IFO 3263) using the process of conjugation, enabling the recipient *A. cerinus* to produce 2-KLG from glucose at a level of 4.5 g/l [see Example 5(c)(2)].

Organisms are however, known which effect the conversion of glucose or other ordinary metabolic substrate, such as, for example, galactose or fructose into 2,5-DKG. Another group of organisms is known which effects the conversion of the 2,5-DKG into 2-KLG, the latter conversion, of course, being catalyzed by a single enzyme within that organism, but utilizing the power of that organism to supply reducing equivalents.

One approach to producing a single organism conversion that is included in this invention comprises construction of an expression vector for 2,5-DKG reductase as outlined above, and transfer of this vector by any of the gene transfer methods mentioned above such as transformation, transduction or conjugation, into cells which are capable of the initial conversion of ordinary metabolites into the 2,5-DKG substrate for this enzyme. As outlined in Example 1 below, this gene transfer results in a single organism 2-KLG factory. The details of the vector construction, gene transfer, and use of the resultant organism are described in the specification.

An alternative approach is to clone the genes encoding the enzymes known to effect the conversion of glucose or other ordinary metabolite to 2,5-DKG from the organisms known to contain them, to construct expression vectors containing these cloned gene sequences, and to transfer such vectors to cells which normally produce the 2,5-DKG reductase. Examples of the enzymes effecting the conversion of an ordinary metabolite to 2,5-DKG are D-glucose dehydrogenase (Adachi, O. et al., Agric. Biol. Chem., 44(2):301–308 [1980] Ameyama, M. et al., Agric. Biol. Chem. 45[4]:851–861 [1981]), D-gluconate dehydrogenase (McIntire, W. et al., Biochem. J., 231:651–654 [1985]; Shinagawa, E. et al., Agric. Biol. Chem. 40[3]:475–483 [1976]; Shinagawa, E. et al., Agric. Biol. Chem. 42[5]:1055–1057 [1978]), 5-keto-D-gluconate dehydrogenase and 2-keto-D-gluconate dehydrogenase (Shinagawa, E. et al., Agric. Biol. Chem., 45(5):1079–1085 [1981]). A third approach is to transfer to a neutral host the entire sequence of enzymes comprising the conversion of an ordinary metabolite to 2-KLG. This last approach offers the advantage of choice of host organism almost at will, for whatever desirable growth characteristics and nutritional requirements it may have. Thus, the use as host cells of organisms which have the heritage of a reasonable history of experience in their culture and growth, such as *E. coli* and Bacillus, confers the advantage of uniformity with other procedures involving bacterial production of enzymes or substrates.

Once the organism capable of carrying out the conversion has been created, the process of the invention may be carried out in a variety of ways depending on the nature of the construction of the expression vectors for the recombinant enzymes and upon the growth characteristics of the host. Typically, the host organism will be grown under conditions which are favorable to production of large quantities of cells. When a large number of cells has accumulated, the promoter(s) supplied with the recombinant gene sequences either become or are already active, permitting the transcription and translation of the coding sequences. Upon suitable expression of these genes, and hence the presence of the desired catalytic quantities of enzyme, the starting material such as glucose, is added to the medium at a level of 1–500 g/L and the culture maintained at 20° C. to about 40° C., preferably around 25°–37° C. for 1–300 hours until conversion to 2-KLG is effected. The starting material concentration may be maintained at a constant level through continuous feed control, and the 2-KLG produced is recovered from the medium either batchwise or continuously by means known in the art.

C. General Methods Emoloved in the Invention

In the examples below, the following general procedures were used in connection with probe construction, screening, hybridization of probe to desired material and in vector construction.

C.1 Probe Preparation

Synthetic DNA probes were prepared by the method of Crea, R. and Horn, T., *Nucleic Acids Res.*, 8: 2231 (1980) except that 2,4,6-triisopropylbenzenesulfonyl-3-nitro-1,2,4-triazole (TPS-NT) was used as coupling agent (de Rooij, J. et al., *Rec. Trav. Chim. Pays-Bas*, 98: 537 [1979]).

C.2 Isolation of Plasmids, Cleavage with Restriction Enzymes

Plasmids were isolated from the identified cultures using the cleared lysate method of Clewell, D. B. and Helinski, *Biochemistry* 9: 4428 (1970), incorporated herein by reference, and purified by column chromatography on Biorad A-50 Agarose. Smaller amounts (minipreps) were prepared using the procedure of Birnboim, H. C. *Nucleic Acids Research* 7: 1513 (1979).

Fragments of the cloned plasmids were prepared for sequencing by treating about 20 μg of plasmids with 10 to 50 units of the appropriate restriction enzyme or sequence of restriction enzymes in approximately 600 μl solution containing the appropriate buffer for the restriction enzyme used or sequence of buffers; each enzyme incubation was at 37° C. for one hour. After incubation with each enzyme, protein was removed and nucleic acids recovered by phenol-chloroform extraction and ethanol precipitation. Alternatively, plasmids were fragmented by DNAase I digestion in the presence of $MnCl_2$ (Anderson, S., Nucleic Acids Res. 9, 3015 [1981] or by sonication (Deininger, P.L., Analyt. Biochem. 129, 216 [1983]). After cleavage, the preparation was treated for one hour at 37° C. with 10 units Klenow DNA polymerase or T4 DNA polymerase in 100 μl of Klenow buffer (50 mM KPi, pH 7.5, 7 mM $MgCl_2$, 1 mM BME), containing 50 nmol dNTP. Protein was removed and nucleic acids recovered as above, and the nucleic acids suspended in 40 μl of loading buffer for loading onto 6 percent polyacrylamide gel, as described above, for sizing. (Alternatively, fragments may be cloned directly into an M13 vector).

DNA sequencing was performed by the dideoxynucleotide chain termination method (Sanger, F. et al. Proc. Natl. Acad. Sci. U.S.A. 74, 5463 (1977)) after cloning the fragments in an M13-derived vector (Messing et al. Nucleic Acids Res. 9, 309 (1981)).

C.3 Ligation Procedures

DNA fragments, including cleaved expression plasmids were ligated by mixing the desired components (e.g. vector fragment cut from 0.25 μg plasmid is mixed with insert cut from 1 μg of plasmid in 20 μl reaction mixture) which components were suitably end tailored to provide correct matching, with T4 DNA ligase. Approximately 10 units ligase were required for μg quantities of vector and insert components. The resulting plasmid vectors were then cloned by transforming E. coli K12 strain 294 (ATCC 31446) or DH-1 (ATCC 33849). The transformation and cloning, and selection of transformed colonies, were carried out as described below. Presence of the desired sequence was confirmed by isolation of the plasmids from selected colonies, and DNA sequencing as described below.

The following examples serve to illustrate but not to limit the invention:

EXAMPLE 1

Recombinant 2,5-DKG Reductase

A. Probe Design

The Tm of the Corynebacterium sp. (ATCC 31090) DNA was measured and found to be 81.5° C. in 7.5 mM sodium phosphate, 1 mM EDTA (pH 6.8). This corresponds to a G+C content of 71 percent, using Pseudomonas aeruginosa DNA (Tm=79.7° C. G+C=67 percent) as a standard. Hence, in synthesis of the probes, those codons known to be prevalent in bacterial DNAs of high G+C content (Goug. M., et al., Nucleic Acids Res. 10: 7055 [1982]) were employed: phe TTC; lys, AAG; val, GTG; pro, CCG; ala, GCC; asp, GAC; gln, CAG; arg, CGC; glu, GAG; asn, AAC; ser, TCC; ile, ATC; leu, CTG; gly, GGC; tyr, TAC. The amino acid sequence of the 2,5-DKG reductase from Corynebacterium sp., (ATCC 31090) shows that the purified enzyme contains a single N-terminal sequence ($\mu$=undetermined)

thr val pro ser ile val leu asn asp gly asn ser ile pro gln leu gly tyr gly val phe lys val pro pro ala asp ala gln arg ala val glu glu ala leu glu val gly tyr $\mu$ his ile asp $\mu$ ala $\mu$ $\mu$ tyr gly (See European Patent Application No. 84304277.1). This sequence and the above codons were used to construct suitable probes, using the method of Anderson and Kingston (Proc. Natl. Acad. Sci. USA 80: 6838 [1983]). Two 43 mers were synthesized by the phosphotriester method of Crea, R. et al., Nucleic Acids Res., 2331 (1980): 5'GGCCTCCTCCACGGCGCGCTGGGCGTCGG-CCGGCGGCACCTTG3'; and, 5'CTCCATCCC-GCAGGTGGGCTACGGCGTGTT-CAAGGTGCCGCCCG3'. The oligonucleotide probes are phosphorylated with 100 $\mu$Ci [$\gamma$-$^{32}$P] ATP (5,000 Ci/mmole, Amersham) and polynucleotide kinase (P-L Biochemicals).

B. Construction of a Plasmid Genomic Library

Genomic DNA was isolated from Corynebacterium sp. ATCC 31090 by the method of Schiller et al., Antimicro. Agents Chemotherapy 18: 814 (1980). Large fragments (>100 kb) were purified by CsCl density gradient centrifugation and partially digested with Sau 3A. The digest was size fractionated by agarose gel electrophoresis into size classes of 1-2 kb, 2-3 kb, 3-4 kb, and 4-6 kb. A genomic library was prepared from each size class of DNA fragments using the vectors pBR322 and pACYC184 (Bolivar, F. et al., Gene 2: 95 [1977]; Chang, A. C. Y., and Cohen, S. N., J. Bacteriol. 134: 1141 [1978]) by cleavage of the BamHI site and insertion of the Sau3A fragments using T4 DNA ligase. The resulting plasmids were used to transform a recA$^-$ derivative of E. coli strain MM294. (ATCC 31446) or DH-1 (ATCC 33849) employing the transformation protocol of D. Hanahan (J. Mol. Biol., 166: 557 (1983)), incorporated herein by reference. Each genomic library contained $10^4$-$10^5$ independent recombinants. In an alternative procedure, additional plasmid libraries were prepared in pBR322 using BamHI fragments (size range 2.0-2.5 Kb) and Pst fragments (size range 0.5-1.5 Kb) of Corynebacterium sp. (ATCC 31090) DNA.

C. Screening of the Plasmid Library in E. coli

The colonies were picked into microtiter dishes, incubated overnight, and stamped onto nitrocellulose filters (BA85) placed on LB plates containing ampicillin or chloramphenicol. The remaining portions of the colonies in the microtiter dishes were preserved by adding 25 $\mu$l of 42 percent DMSO and storing at $-20°$ C.

The transferred portions of the colonies were incubated for 8 to 9 hours at 37° C. and amplified by transferring the filters to plates containing 12.5 $\mu$g/ml chloramphenicol or spectinomycin and incubating at 37° C. overnight.

The plasmid library in E. coli is screened by filter hybridization. The DNA is denatured and bound to duplicate filters as described by Itakura, K. et al., Nucleic Acids Res. 9: 879-894 (1981). The filters for hybridization are wetted in about 10 ml per filter of 5X SET, 5X Denhardt's solution and 50 $\mu$g/ml denatured salmon sperm DNA, and 0.1 percent sodium pyrophosphate+20 percent formamide (5X SET=50 mM Tris-HCl [pH 8.0]. 5 mM EDTA, 500 mM NaCl; 5X Denhardt's solution=0.1 percent bovine serum albumin, 0.1 percent polyvinylpyrrolidone, 0.1 percent Ficoll; see Denhardt, Biochem. Biophys. Res Comm. 23: 641 [1966]). The filters are prehybridized with continuous agitation at 42° for 14-16 hrs, and probed with $\sim 1\times 10^8$ cpm of probe as prepared in subparagraph A of this Example at 42° C. The filters that were hybridized with the probes of subparagraph A are washed with 0.2×SSC. 0.1 percent SDS, 0.1 percent sodium pyrophosphate at 42° C. for 3×30 min. Each of the duplicate filters is blotted dry, mounted on cardboard and exposed to Kodak XR5 X-Ray film with Dupont Cronex 11R Xtra life Lightning-plus intensifying screens at $-70°$ C. for 4-24 hrs.

Cells from positive colonies were grown up and plasmid DNA was isolated by the method of Clewell and Helinski (Proc. Natl. Acad. Sci. U.S.A. 62: 1159 [1969]). DNA was fragmented with AluI and PstI and subcloned into the vectors M13mp8 and M13mp9 (Messing, J. and Viera, J., Gene 19:269 [1982]). Subclones that hybridized to the probes were sequenced using the dideoxy chain termination procedure (Sanger, F. et al., Proc. Natl. Acad. Sci. U.S.A. 74: 5463 [1977]) in order to verify that the DNA coded for the 2,5-DKG reductase. Those clones which hybridized to the probes were arbitrarily labelled pDKGR2 and pDKGR9. pDKGR2 clones contained a 2.2 Kb BamHI fragment of the 2,5-DKG reductase gene pDKGR9 clones contained a 0.88 Kb PstI fragment of the 2,5 DKG reductase gene.

D. Construction of Expression Vectors for 2,5-DKG Reductase

The 2,5-DKG reductase gene, accompanied by either its own or a synthetic ribosome binding site, is inserted 'downstream' of the E. coli trp (or tac) promoter or the pACYC184 CAT promoter on expression plasmids, which also contain a tetracycline resistance gene or other selectable marker, and an origin of replication derived from plasmids ColEl. 15A, or RSF1010. Some constructs may contain, in addition, an active gene coding for *E. coli* trp repressor or the *E. coli* lac repressor which allows the expression of the 2,5-DKG reductase gene to be regulated by exogenously added indole acrylic acid or isopropylthio-β-galactoside (IPTG). Various mutated versions of the above plasmids are also employed for the expression of 2,5-DKG reductase.

Figure 1:
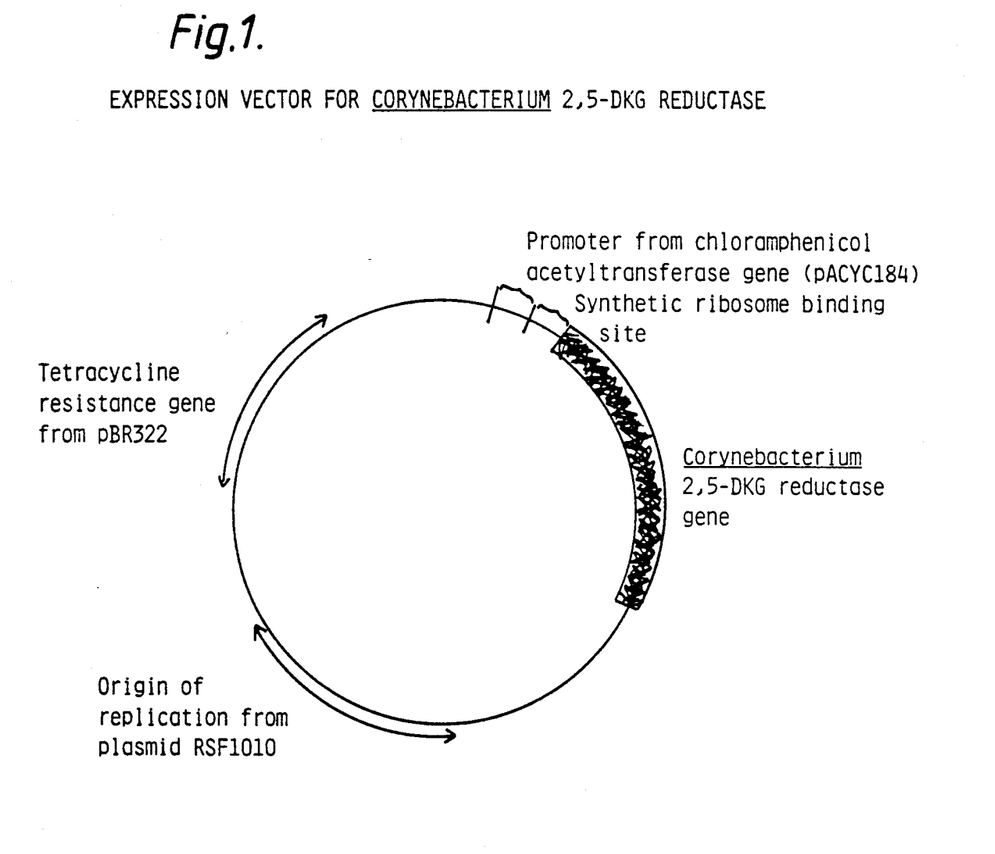
FIG. 1 shows an expression vector for the 2,5-DKG reductase gene.
Figure 2:
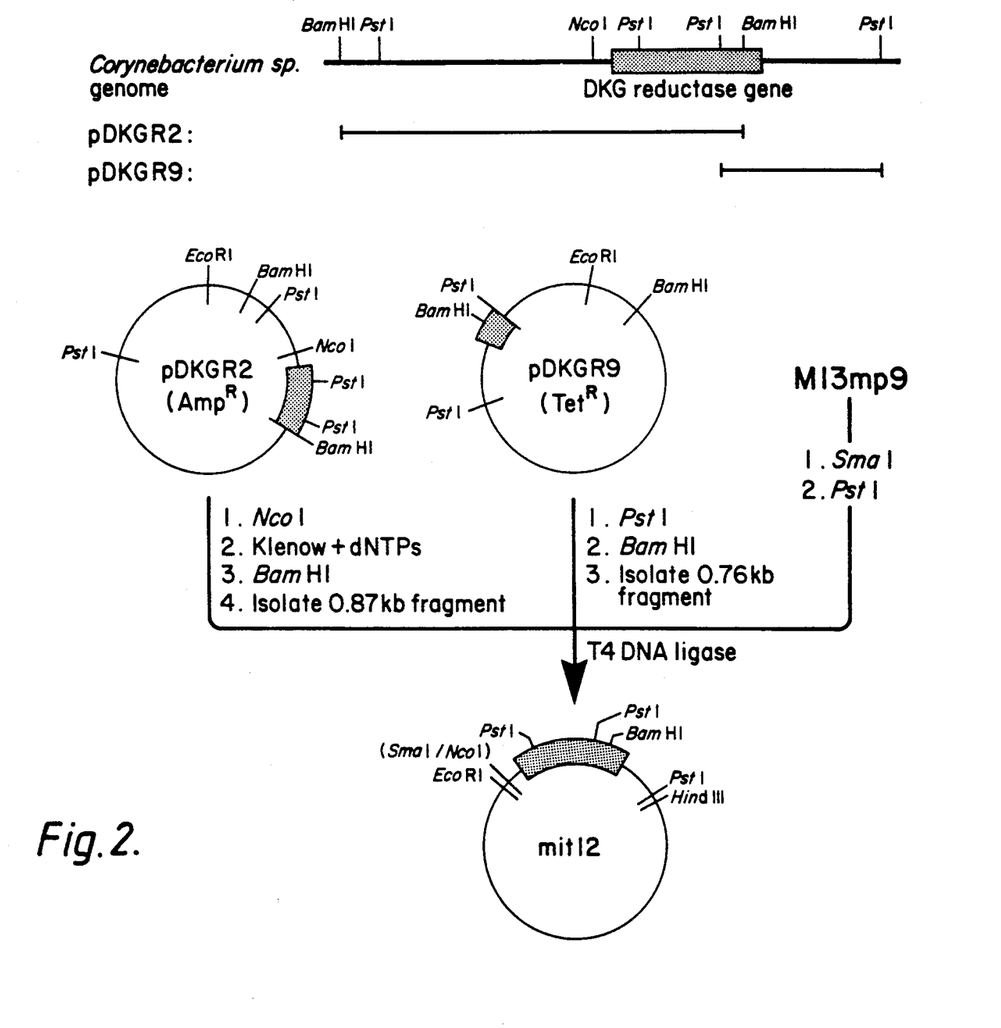
FIGS. 2 and 3 show the construction of an alternative expression vector for the 2,5-DKG reductase gene.

A cloned 2.2 Kb BamHI fragment of *Corynebacterium* sp (ATCC 31090) DNA, containing a portion of the 2,5-DKG reductase gene, was isolated with the 43-mer probes as described above. An 0.12 Kb PstI/BamHI fragment of this plasmid was further used as a probe to isolate an overlapping 0.88 Kb PstI fragment of *Corynebacterium sp* DNA, which contained the rest of the gene. As described in FIG. 2, pDKGR2 (containing the 2.2 Kb BamHI fragment) was digested with NcoI, treated with *E. coli* DNA polymerase I Klenow fragment and dNTPs to create flush-ended DNA, then further digested with BamHI to release an 0.87 Kb fragment; this fragment was purified by electrophoresis on low-melting-point agarose. The plasmid pDKGR9 (containing the 0.88 Kb PstI fragment) was digested with PstI and BamHI, and the resultant 0.76 Kb fragment similarly isolated on low-melting-point agarose. The 0.87 Kb NcoI/BamHI fragment and the 0.76 Kb BamHI/PstI fragment were then combined with SmaI/PstI - digested M13mp9 and ligated to yield an M13 recombinant ("mit12") with a 1.6 Kb insert of *Corynebacterium* sp DNA containing the entire 2,5-DKG reductase gene (FIG. 2).

Figure 3:
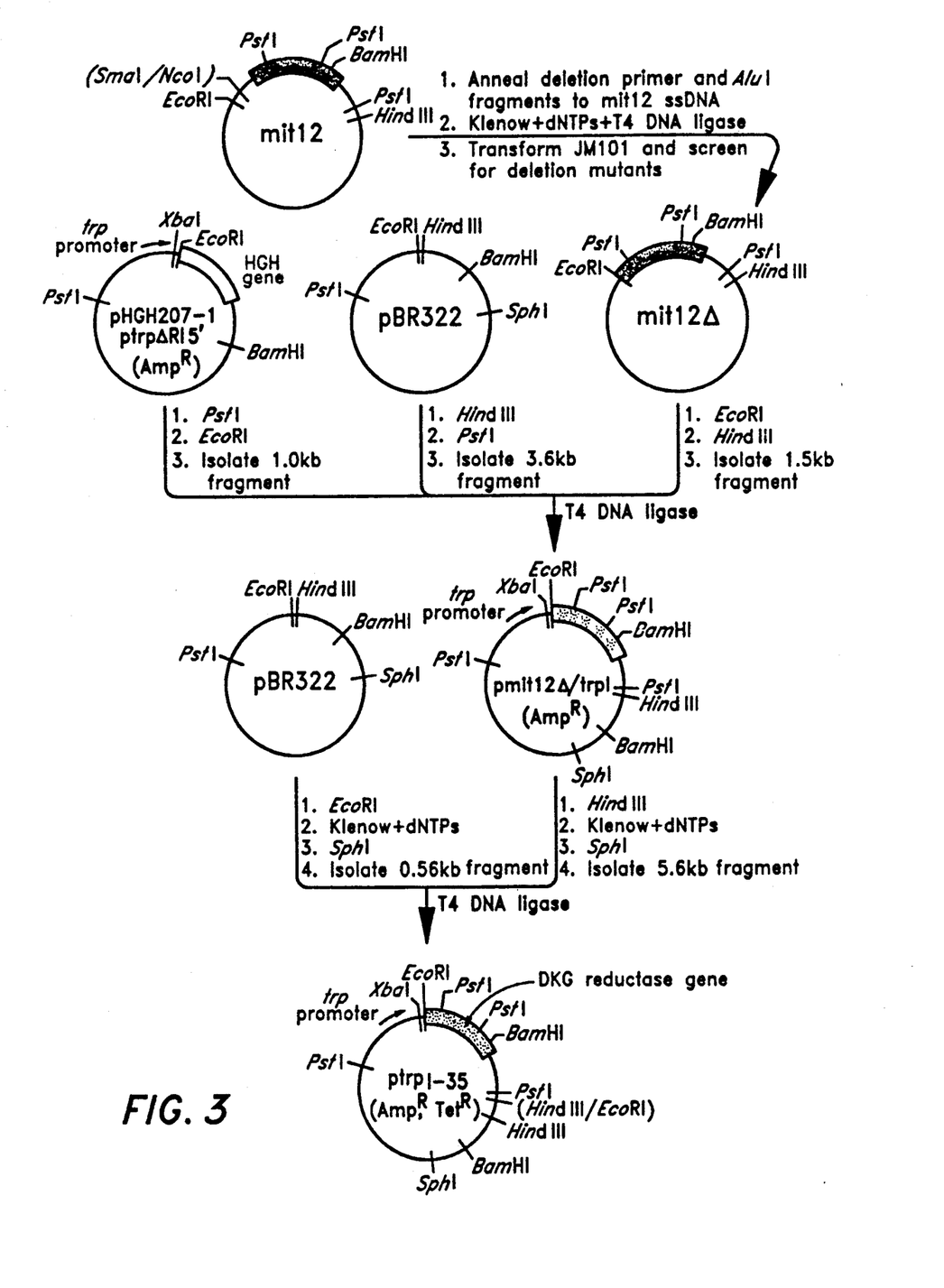

To mit12 single-stranded DNA a "deletion primer" (sequence: ACGGCCAGTGAATTCTATGACAGTTCCCAGC) and AluI fragments of M13mp9 DNA were annealed. This template-primer combination was then treated with *E. coli* DNA polymerase Klenow fragment in the presence of dNTPs and T4 DNA ligase to create in vitro heteroduplex mit12 RF molecules, as described by Adelman et al., DNA 2: 183 (1983). These molecules were used to transform the host JM101 (Messing, J. Recomb. DNA Tech. Bull 2:43 [1979]), and recombinant phage incorporating the desired deletion were detected by plaque hybridization using the deletion primer as a probe (Adelman et al., DNA 2:183 [1983]). This construction was designated mit12Δ (FIG. 3).

Figure 4:
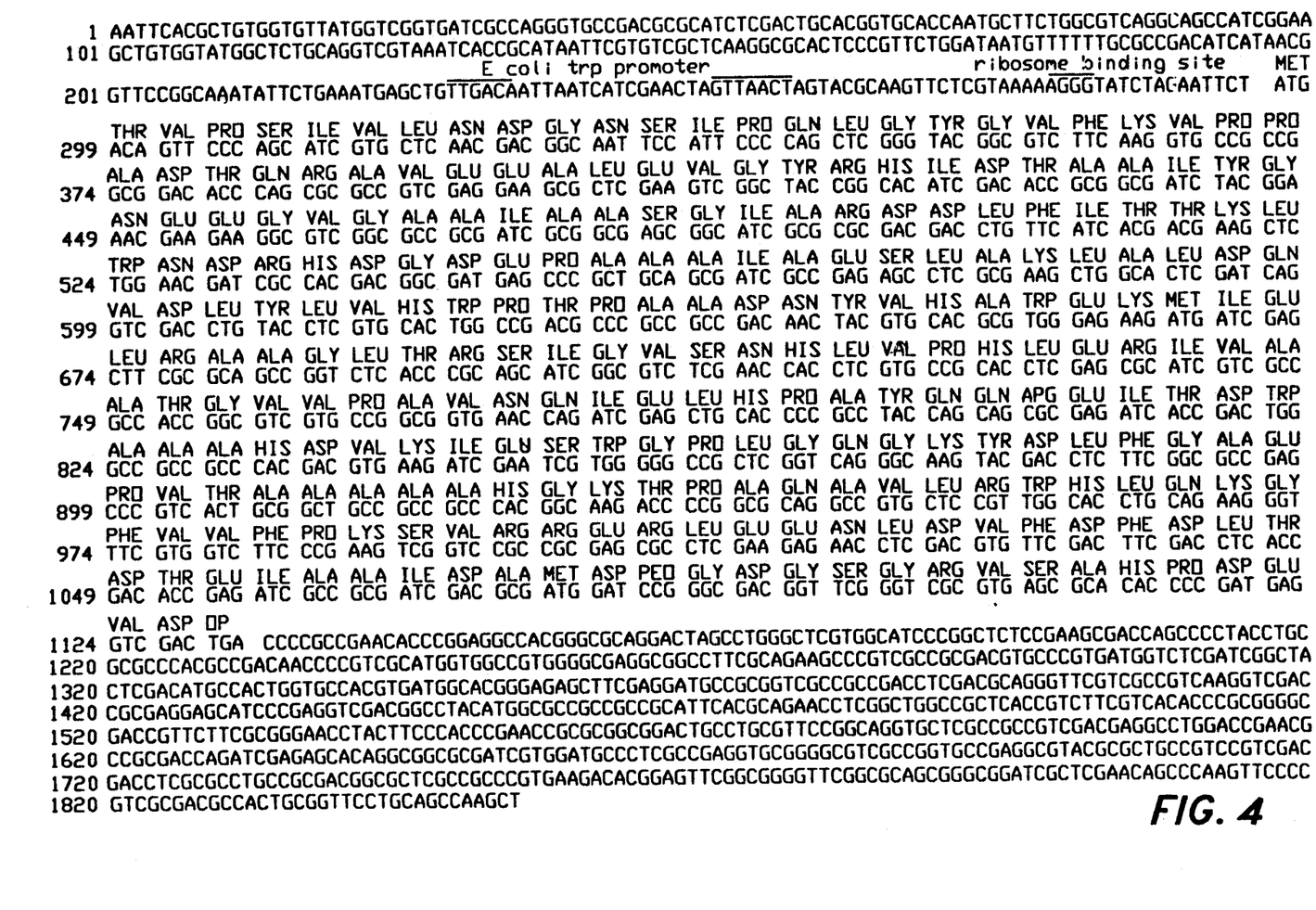
FIG. 4 shows a sequence including the 2,5-DKG reductase gene and control regions of the pTrpl-35 expression vector.

The mit12Δ RF DNA was digested with EcoRI and HindIII to yield a 1.5 Kb fragment containing the 2,5-DKG reductase gene. The human growth hormone expression plasmid, pHGH207-1ptrpΔRI5' (pHGH207-1ptrpΔRI5. is a derivative of pHGH207-1 [de Boer et al., Proc. Natl. Acad. Sci. U.S.A. 80: 21 (1983)] in which the EcoRI site between the ampicillin resistance gene and the trp promoter has been deleted), was digested with EcoRI and PstI to yield a 1.0 Kb fragment containing the *E. coli* trp promoter. pBR322 was digested with PstI and HindIII to yield a 3.6 Kb fragment. These three fragments were ligated together to form an expression plasmid for 2,5-DKG reductase, designated pmit12Δ/trpl (FIG. 3). This plasmid was unable to confer tetracycline resistance on host cells. A plasmid that would encode a complete tetracycline resistance function was constructed as follows: pmit12Δ/trpl DNA was digested with HindIII, treated with *E. coli* DNA polymerase I Klenow fragment and dNTPs to produce flush ended DNA, then digested with SphI; the resultant 5.6 Kb fragment was purified by electrophoresis on low melting agarose. Similarly, pBR322 DNA was digested with EcoRI, treated with *E. coli* DNA polymerase I Klenow fragment and dNTPs, digested with SphI, and the resultant 0.56 Kb fragment purified on low melting agarose. The 5.6 Kb and 0.56 Kb fragments were then ligated together to yield a tetracycline-resistant 2,5-DKG reductase expression plasmid designated ptrpl-35 (FIG. 3). The DNA sequence of the trp promoter, synthetic ribosome binding site, and 2,5-DKG reductase gene contained on this plasmid is shown in FIG. 4.

E. Production of Recombinant 2,5 DKG reductase by *Erwinia herbicola*

Cells are prepared for transformation by the method of Lacy and Sparks, *Phytopathological Society*, 69: 1293-1297 (1979). Briefly a loop of suitable host cells, *Erwinia herbicola* (ATCC 21998), or *E. coli* MM294 (ATCC 314646), is inoculated into 5 ml of LB medium and incubated at 30° C. for 14-16 hrs. A 1:100 dilution of this overnight growth is inoculated into LB, the culture grown to $OD_{590}$ of 0.4, and the cells recovered by centrifugation at 4° C. The pellet was resuspended in ½ volume of 10 mM NaCl, again centrifuged at 4° C., the pellet resuspended in an equal volume of 30 mM $CaCl_2$, and after 60 minutes at 0° C., the cells again centrifuged at 4° C. The pellet is resuspended in 1/12 volume of 30 mM $CaCl_2$ and stored at 4° C. overnight. (Alternatively, cells may be resuspended in 30 mM $CaCl_2$, 15 percent glycerol, and stored at −70° C.)

Transformation is effected by incubation of 1 μg plasmid in 0.2 ml of competent cells at 0° C. for 2 hr followed by heating to 42° C. for 1 min. 3 ml of LB broth is added and cells are allowed to recover for 4 hrs at 37° C., then cells are plated on selective medium as described by Lacy and Sparks (supra). Successful transformants are grown on LB broth to a density of O.D.550=1.0, then centrifuged and resuspended in minimal medium in the presence of 0.2 percent glucose. IAA or IPTG is then added to the medium, and after 0.5-1.0 hrs the cells recovered by centrifugation and lysed by treatment with lysozyme and a detergent (Tween 80).

Figure 5:
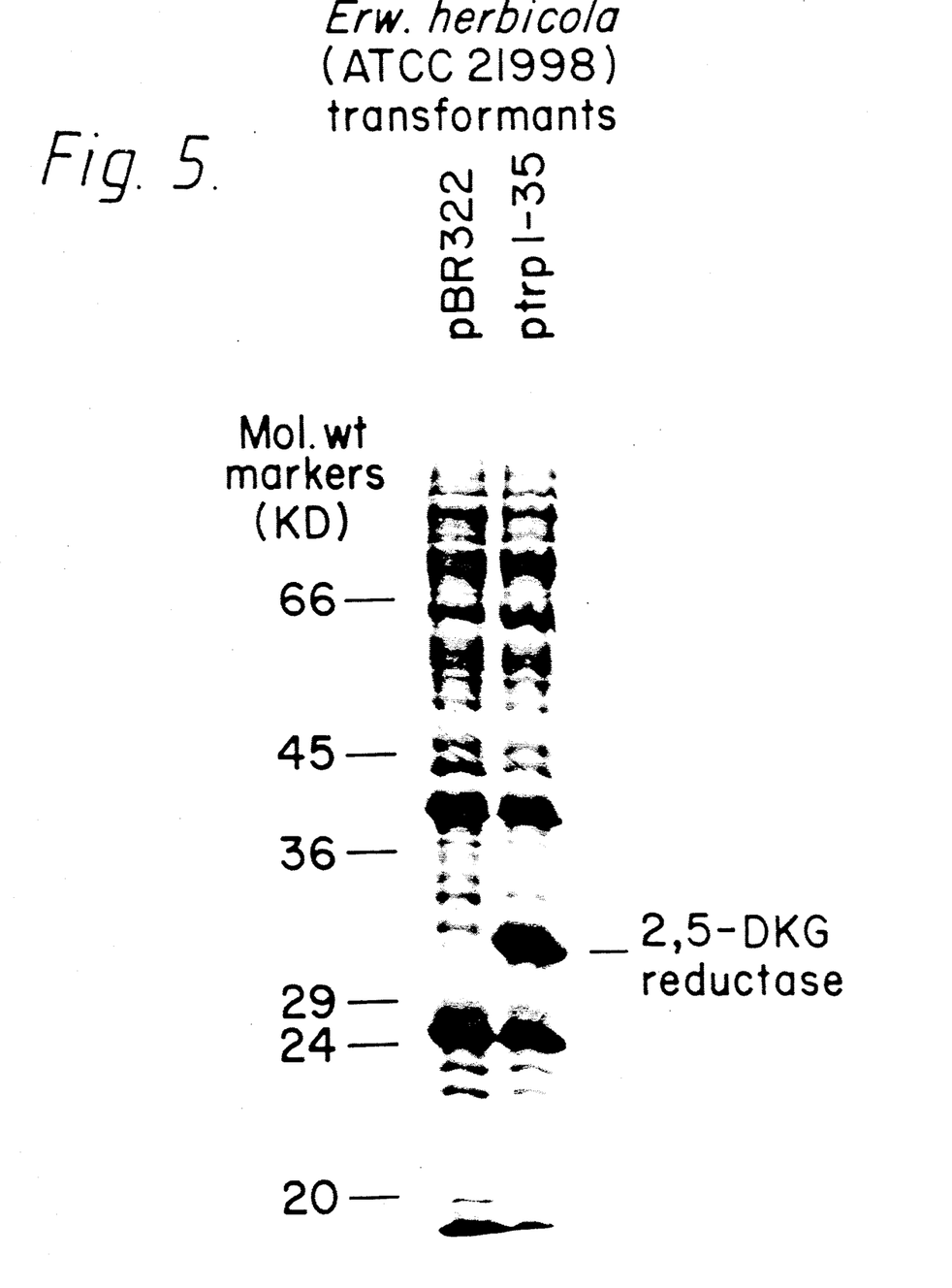
FIG. 5 shows a stained gel of a protein extract from *Erwinia herbicola* (ATCC 21998) transformed with the 2,5-DKG reductase expression vector having the sequence of FIG. 4.

The supernatant is assayed for the presence of 2,5-DKG reductase and the results are shown in Table I. The proteins were analyzed by SDS polyacrylamide gel electrophoresis (FIG. 5). The protein band representing the recombinant 2,5-DKG reductase was identified immunologically using the Western blotting procedure (Tobin, H. et al., Proc. Natl. Acad. Sci. U.S.A. 76, 4350 [1979]).

TABLE I

| Extract | 2.5-DKG reductase activity (Δ Absorbance (340 nm) min.$^{-1}$/100 μL) |
|---|---|
| pBR322 transformed *Erwinia herbicola* (ATCC 21998) | −0.087 |
| ptrpl-35 transformed *Erwinia herbicola* (ATCC 21998) | −1.925 |

EXAMPLE 2

Production of 2-KLG by Contacting Recombinant Organism with 2,5-DKG

Cells of ptrpl-35 transformed *Erw. herbicola* (ATCC 21998) were streaked from a frozen glycerol stock onto LB solid medium (10 g/L tryptone, 5 g/L yeast extract, 10 g/L NaCl, 15 g/L agar) containing 5 mg/L tetracycline, then incubated 48 hrs at 30° C. A single colony was picked and used to inoculate 5 ml of LB liquid medium containing 5 mg/L tetracycline, and this was shaken in a test tube for 16 hrs at 30° C. 1.0 ml of this culture was used to inoculate 100 ml LB liquid medium containing 5 mg/L tetracycline, and this was then shaken at 200 rpm for 16 hrs at 30° C. Cells were harvested by centrifugation washed once in an equal volume of fresh LB medium, then resuspended in 50 ml of LB medium containing 5 mg/L tetracycline and 20 g/L 2,5-DKG. A 10 ml aliquot of this was shaken in a 125 ml flask at 200 rpm for 16 hrs at 30° C. The resultant broth was analyzed by HPLC and found to contain 2.0 g/L of 2-KLG. A control culture containing pBR322-transformed Erw. herbicola (ATCC 21998), treated in a similar fashion, contained no 2-KLG.

EXAMPLE 3

Production of 2-KLG from Glucose by Recombinant Organism

Cells of ptrpl-35-transformed Erw. herbicola (ATCC 21998) were streaked from a frozen glycerol stock onto LB solid medium (10 g/L tryptone, 5 g/L yeast extract, 10 g/L NaCl, 15 g/L agar) containing 5 mg/L tetracycline, then incubated for 48 hrs at 30° C. A single colony was picked and used to inoculate 5 ml of LB liquid medium containing 5 mg/L tetracycline, and this was shaken in a test tube for 16 hrs at 30° C. 1.0 ml of this culture was used to inoculate 100 ml of ATCC medium 1038 (3.0 g/L glucose, 5.0 g/L yeast extract, 5.0 g/L peptone, 7.5 g/L $CaCO_3$, pH 7.0) containing 5 mg/L tetracycline, and this was shaken at 200 rpm in a 500 ml flask at 30° C. for 16 hrs. Cells from 75 ml of this culture were then harvested by centrifugation, resuspended in 50 ml of fresh ATCC medium 1038 containing 5 mg/L tetracycline and 20 g/L glycerol, and shaken at 200 rpm in a 500 ml flask at 30° C. for 48 hrs. The resultant broth was analyzed by HPLC and GC/MS and found to contain 1.0 g/L 2-KLG. A control culture containing pBR322-transformed Erw. herbicola (ATCC 21998), treated in a similar fashion, contained no 2-KLG.

EXAMPLE 4

Production of 2-KLG by Erwinia herbicola in Different Media

The following experiment was performed to demonstrate the production of 2-KLG from readily available carbon sources.

The production of 2-KLG by Erwinia herbicola (ATCC 21998)/ptrpl-35 was accomplished by growing the cells in a medium containing the following:

| Yeast Extract (Nestles) | 10 g/l |
| Calcium Carbonate | 20 g/l |
| Corn Steep Liquor | 10 g/l |
| Glucose | 20 g/l |
| Tetracycline | 5 mg/l |

The glucose and the tetracycline were sterilized separately and added prior to inoculation.

An inoculum was prepared by adding 1.0 ml of a frozen stock culture to 50 ml of Luria broth containing 5 g/l glucose and 5 mg/l tetracycline. The 250 ml baffled flask containing the inoculum was incubated at 30° C. for 12 hours with shaking.

A 250 ml baffled flask was filled with 50 ml of the production medium above and inoculated with 1 ml of the inoculum The flask was incubated with shaking at 30° C. The pH of the medium at the time of inoculation was 5.1 due to the acidity of corn steep liquor. After 57 hours the pH had risen to 8.71 and 2-KLG was shown to be present at a concentration of 0.6 mg/ml by HPLC. The presence of 2-KLG was confirmed by HPLC and GC-Mass Spectrometry.

EXAMPLE 5

Production of Recombinant 2,5 DKG reductase by Acetobacter cerinus

Conjugal transfer of RP4::Mu from E. coli to Acetobacter suboxydans was reported by Murooka, Y. et al., J. Bacteriol. 145(1):358 (1981). Triparental mating of E. coli QSR39, E. coli 294 and Acetobacter cerinus was used to transfer the foreign plasmid DNA. Inoue, T. et al., J. Ferment. Tech. 63(1):1-4 (1985) subsequent to this invention describe a similar method. Conjugal transfer or mating was used to improve the efficiency of transformation of Acetobacter cerinus. Conjugal transfer efficiency has varied with various acetic acid bacteria. (See Murooka et al., supra and Inoue et al., supra.) $CaCl_2$-mediated transformation has also been used to introduce plasmid DNA into Acetobacter aceti. (Okumara, H. et al., Agric. Biol. Chem. 49[4]:1011 [1985]; Fukaya, M. et al., Agric. Biol. Chem. 49[7]:2083 [1985]; and Fukaya, M. et al., Agric. Biol. Chem. 49[7]:2091 [1985]).

E. coli QSR39 (lei−, Bl−, R−M−, SuP+, Tp$^r$, Tra+) containing the Inc P-1 plasmid R751 (Tp, Tra+) was used. (Meyer, R. J. and Shapiro, J. A., J. Bacteriol. 143: 1362–1373 [1980] and Johanpatia, R. S. and Dotta, N., J. Med. Microbiol. 7:169 [1974]). Also a nalidixic acid resistant strain of Acetobacter cerinus (IFO 3263) was isolated by plating 0.1 ml of a saturated culture of Acetobacter cerinus on mannitol plates containing 20 γ/ml nalidixic acid.

A. Plasmid Constructions (1) R751 is a 50 Kb plasmid containing tra (transfer) gene. The tra gene products permit conjugal transfer of the 143 plasmid. R751 has been described by Meyer, R. J. and Shapiro, J. A., J. Bacteriol. 143: 1362–1373 (1980).

(2) Plasmid 143 contains the E. coli trp promoter, a synthetic ribosome binding site, and the Corynebacterium 2,5-DKG reductase gene and the tetracycline resistance gene from plasmid pBR322 inserted at the EcoRI site of plasmid RSF1010 (Bagdasarian et al., Gene 16:237–247 [1981] and Guerry, P. et al., J. Bacteriol. 117:619 [1974]).

Figure 6:
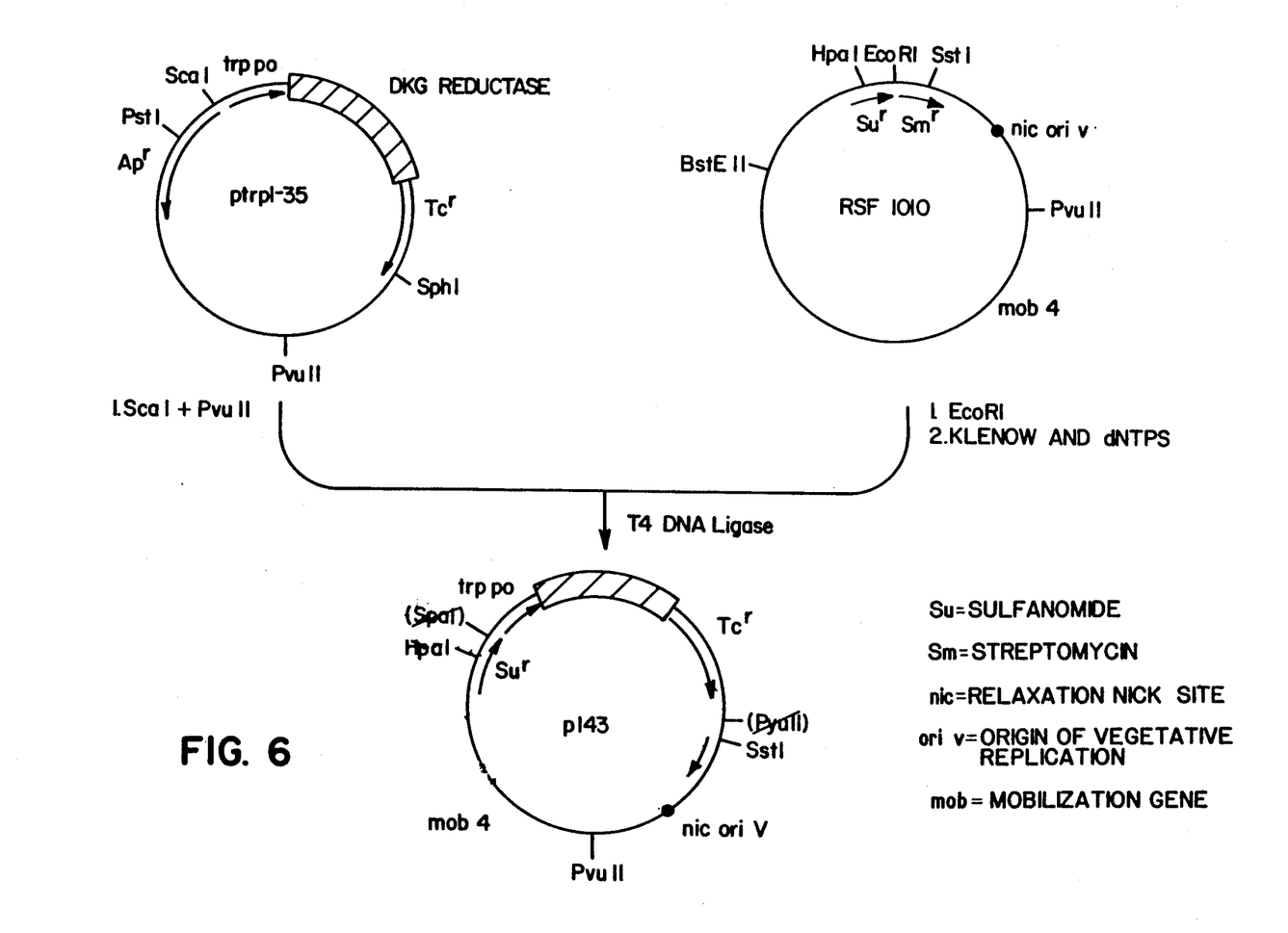
FIG. 6 shows the construction of plasmid 143 containing the trp promoter and 2,5-DKG reductase gene.

(3) RSF 1010 is a broad host range plasmid (Inc Q) able to replicate in a wide range of gram.negative bacteria. Plasmid RSF 1010 was digested with EcoRI. After the digestion was complete the EcoRI site was filled in by treating the DNA with 5 mM dNTPs and the Klenow fragment of Pol I. Plasmid ptrpl-35 was digested with ScaI and PvuII to produce a blunt-ended linear DNA fragment containing the Corynebacterium 2,5-DKG reductase gene under the control of the E. coli trp promoter and the tetracycline resistance gene from pBR322 under the control of its own promoter. Both digested DNAs were extracted with phenol/chloroform, ethanol precipitated, and resuspended in $H_2O$. The fragments were ligated together using T4 DNA ligase and used to transform E. coli strain MM294. Plasmid 143 was isolated and the presence of the correct gene sequences verified by restriction analysis and Southern blots (FIG. 6).

B. Bacterial Matinzs

*Acetobacter cerinus* (nal^r strain, isolated as described above) was grown in mannitol broth (25 g/L mannitol, 5 g/L yeast extract, 3 g/L peptone). *E. coli* QSR39 (containing plasmid pR751) was grown in LB broth containing 2.5 µg/ml trimethoprin. *E. coli* MM294 (containing plasmid p143) was grown in LB broth containing 5 µg/ml tetracycline.

0.5 ml of 0.6 OD$_{590}$ cultures of *Acetobacter cerinus, E. coli* MM294 (containing plasmid 143), and *E. coli* QSR39 (containing plasmid R751) were mixed and filtered onto a pre-moistened nitrocellulose membrane (0.45 µm pore size). The filter was incubated face-up on LB solid agar overnight at 27° C.

The filter was then placed in a sterile tube and its surface was rinsed with 1.0 ml mannitol broth with 10 γ/ml tetracycline and 10 γ/ml nalixidic acid. 100 µl, 10 µl and 0.5 µl were plated on mannitol solid agar plates containing 10 γ/ml tetracycline and 10 µg/ml nalidixic acid. The plates were incubated at 27° C. overnight.

Colonies that appeared on the plates were restreaked on YGC (50 g/L glucose, 5 g/L yeast extract, 12.5 g/L CaCO$_3$) solid agar plates containing 10 γ/ml tetracycline. *Acetobacter cerinus* transconjugants were identified as those that were tetracycline resistant and acid-producing (as determined by clear halo production). One of these, termed *Acetobacter cerinus* (p147), was chosen for further characterization.

A plasmid prep from *Acetobacter cerinus* (p147) was prepared and analyzed by restriction mapping and Southern blotting. This analysis showed that *Acetobacter cerinus* (p147) contained an RSF1010-based plasmid encoding the 2,5-DKG reductase gene that was indistinguishable from plasmid 143, indicating that plasmid transfer from *E. coli* had occurred.

Figure 7:
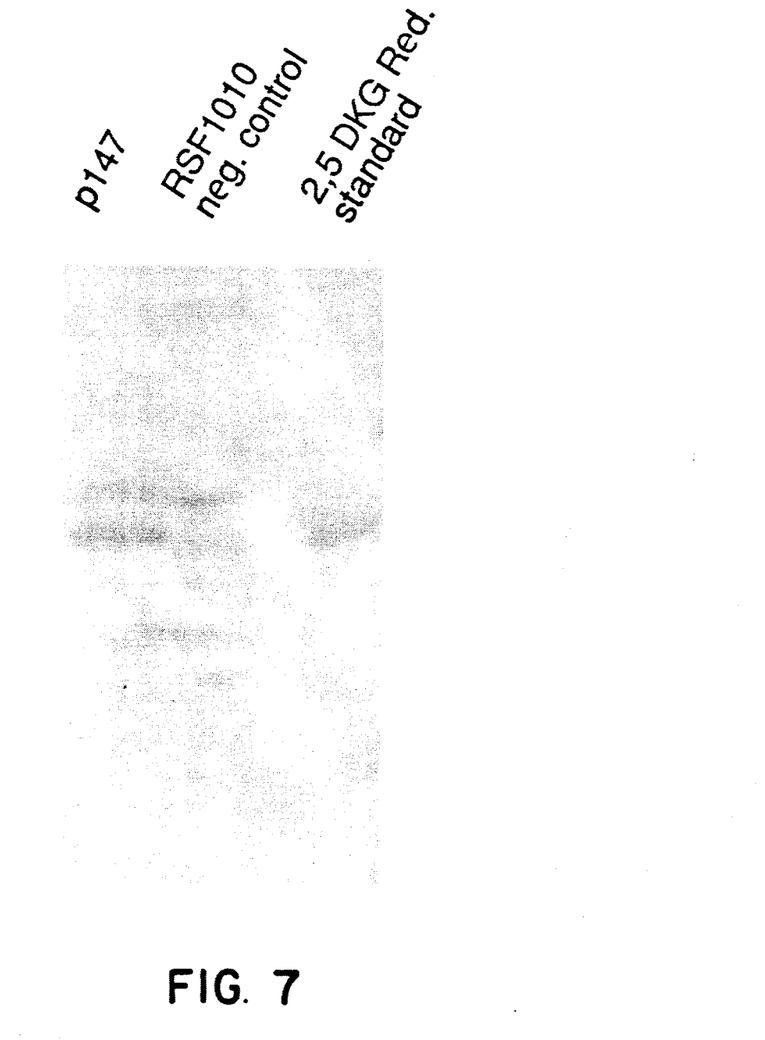
FIG. 7 - SDS gel of protein extract from lysed *Acetobacter cerinus* IFO 3263 transformed by conjugal transfer with the 2,5 DKG reductase expression vector p143. The p143 plasmid in *A. cerinus* is referred to as p147.

The supernatant was assayed for the presence of 2,5-DKG reductase using methods known to the ordinarily skilled artisan and the proteins analyzed by SDS polyacrylamide gel electrophoresis (FIG. 7). The protein band representing the recombinant 2,5-DKG reductase was identified immunologically using the Western blotting procedure (Tobin, H. et al., Proc. Natl. Acad. Sci. U.S.A. 76: 4350 [1979]).

An alternative mating procedure that did not require preselection of an Acetobacter cerinus IFO3263 nalidixic acid-resistant strain was also used. This procedure takes advantage of the vitamin B1 requirement of the p143 *E. coli* host strain, MM294, and the fact that *Acetobacter cerinus* does not require vitamin B$_1$. The procedure is identical to that described above, except that after the mating has been allowed to proceed on the filter, the cells are plated on minimal glucose or mannitol plates (5 g/L glucose or mannitol 6 g/L Na$_2$HPO$_4$, 3 g/L KH$_2$PO$_4$, 0.5 g/L NaCl, 1 g/L NH$_4$Cl, 1 mM MgSO$_4$, 1 mM CaCl$_2$) containing 0.25 mM nicotinamide and 15 µg/ml tetracycline in order to select for Acetobacter cerinus (p147) transconjugants.

C. Fermentation of Glucose to 2-KLG by *A. cerinus* IFO 3263/p147

C.1 Preparation of the Inoculum

*A. cerinus* 3263 IFO/p147 was cultivated in an aqueous medium containing a carbon source, such as glucose, glycerol, citrate, etc. at a concentration from 1 to 20 g/L. Nitrogen was supplied as inorganic ammonium salts such as ammonium sulphate or ammonium chloride usually in the range of 0.05 to 1 g/L. Alternatively organic nitrogen such as yeast extract, hydrolyzed casein, or urea was used. Minerals were supplied. In many cases minerals contained in an organic nitrogen source such as yeast extract or casamino acids, were sufficient for growth. However, additional magnesium, phosphorous, potassium were included in the medium in the form of salts such as potassium chloride, potassium phosphate, magnesium sulphate or similar salts, generally in amounts from 0.1 to 2.0 grams per liter of medium. Tetracycline HCL was added to the medium in a concentration of 5 to 40 mg/L.

Generally, the Acetobacter strain was introduced into a medium containing the components described above. The microorganism was cultivated for a period of 8 to 24 hours at a temperature of from 25° to 35° C. Oxygen was provided to the inoculum vessel either by shaking or by mechanical agitation and air sparging. The pH was maintained between 5.0 and 7.5 preferably 5.5 to 6.5, with a suitable buffer such as CaCO$_3$, MES (2-(N-Morpholino)-ethanesulphonic acid), or potassium phosphate. Alternatively, the pH could be controlled by addition of acid such as phosphoric or sulfuric and base such as potassium hydroxide or sodium hydroxide.

C.2 Preparation of the Production Medium and Production of 2 KLG from Glucose

A suitable volume, 0.1 to 10%, of *Acetobactor cerinus inoculum* culture is then added to a medium described as the production medium. Glucose is added to the initial culture medium in the concentration of 5 to 20 g/L. Alternatively a small amount of glucose, 2 to 5 g/L, can be added to the initial medium as a substrate for growth and the remainder can be added at a later time, 12 to 36 hours after inoculation, for production of 2-KLG. This medium should contain an organic nitrogen source, such as yeast extract in the concentration of 0.5 to 2 g/L as well as an inorganic nitrogen source such as ammonium sulphate in the concentration of 0.1 to 0.5 g/L. Inorganic elements must also be included in the form of salts as was described for the inoculation medium. Tetracycline HCL was added to the medium at a concentration of from 5 to 20 mg/L. The medium was sterilized using either filtration or autoclaving. Those components which are not stable at autoclaving temperatures such as glucose, MES and tetracycline should be sterilized by filtration and added to the medium separately.

The microorganism was cultivated for a period of 36 to 120 hours at a temperature of from 25° to 35° C. Oxygen was provided to the inoculum vessel either by shaking or by mechanical agitation and air sparging. The pH was maintained between 5.0 and 7.5, preferably 5.5 to 6.5. A buffer was selected which did not interfere with 2-KLG production and which maintained the pH between 4 5 and 7.0, preferably 5.5 to 6.5. Buffers described for the inoculation medium were suitable for the production medium as well but other production buffers are also possible. Alternatively, pH can be controlled by addition of acid such as phosphoric or sulfuric and base such as potassium hydroxide or sodium hydroxide.

The production of 2-KLG was observed using analytical methods previously described.

The following medium was prepared for cultivation of the inoculum:

| | |
|---|---|
| Bacto Tryptone | 10 g/l |
| Bacto Yeast Extract | 5 g/l |
| NaCl | 10 g/l | pH was adjusted to 7.0 using NaOH and HCl.

Volume was raised to 1 L with deionized water and autoclaved for 30 min, 121° C.

A 250 ml baffled erlenmeyer flask containing 30 ml of Luria broth was inoculated with *Acetobacter cerinus* 3263 IFO/p147. The culture was incubated on a rotary shaker (250 rpm, 1.5 inch throw) for 12 hours at 30° C. After this time 0.1 ml of culture was inoculated into the following production medium.

| | |
|---|---|
| $(NH_4)_2SO_4$ | 0.4 g/l |
| $K_2HPO_4$ | 6.0 g/l |
| $KH_2PO_4$ | 4.0 g/l |
| $MgSO_4.7 H_2O$ | 1.0 g/l |
| MES (2-[N-Morpholino]-ethanesulfonic acid) | 13.1 g/l |

These salts were added to distilled water and sterilized by filtration.

| | |
|---|---|
| Yeast Extract | 1.0 g/l |
| Glucose | 5.0 g/l |
| Tetracycline HCl | 20 mg/l |

The pH was adjusted to 7.0 with NaOH. The components Difco Yeast Extract 1.0 g/l and Glucose 5.0 g/l were sterilized separately by autoclaving at 121° C. for 30 min. They were added to the salts medium after all components had cooled to room temperature. After 24 hours 10 g/l additional glucose was added to the fermentation broth.

The glucose was converted to 2-KLG (3.2 to 6.5 g/l) in an overall molar yield of from about 20 to 40% after 96 hours. Cell density reached from 1 to 5 $A_{550}$. The pH of the medium was reduced to between pH 5.0 to pH 6.5, typically pH 6.0.

We claim:

1. A process for converting glucose to 2-KLG which process comprises culturing in a medium containing glucose under suitable metabolic conditions, bacterial cells to which genetic material has been transferred wherein the transfer of said genetic material renders a bacterial host cell capable of converting glucose to 2,5-DKG but lacking the ability to convert 2,5-DKG to 2-KLG, capable of converting 2,5-DKG into 2-KLG.

2. The process of claim 1, wherein the genetic material transferred to the bacterial cells in an expression vector effective in expressing a DNA sequence encoding 2,5-DKG reductase.

3. The process of claim 1 wherein the bacterial cell to which genetic material is transferred is of the genus Erwinia.

4. The process of claim 3 wherein said host cell is *Erwinia herbicola* ATCC 21998.

5. The process of claim 1 wherein the host cell is of the genus Acetobacter.

6. The process of claim 5 wherein the host cell is *Acetobacter cerinus* (IFO 3263).

7. The process of claim 1 wherein the host cell is of the genus Gluconobacter.

8. The process of claim 1 wherein the transfer is by conjugation.

9. A microorganism to which genetic material encoding 2,5-DKG reductase is transferred such that said transfer renders a host cell capable of converting glucose to 2,5-DKG but lacking the ability to convert 2,5-DKG to 2-KLG, capable of effecting the conversion of 2,5-DKG into 2-KLG.

10. The microorganism of claim 9 wherein the genetic material is an expression vector encoding 2,5-DKG reductase.

11. The microorganism of claim 10 which is of the genus Erwinia.

12. The microorganism of claim 9 which is of the genus Acetobacter.

* * * * *